United States Patent
Juul-Mortensen et al.

(10) Patent No.: US 7,632,806 B2
(45) Date of Patent: Dec. 15, 2009

(54) STABILIZED PHARMACEUTICAL PEPTIDE COMPOSITIONS

(75) Inventors: Claus Juul-Mortensen, København V (DK); Dorte Kot Engelund, Holte (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 11/290,634

(22) Filed: Nov. 30, 2005

(65) Prior Publication Data

US 2006/0178304 A1    Aug. 10, 2006

Related U.S. Application Data

(63) Continuation of application No. PCT/DK04/00380, filed on Jun. 3, 2004.

(30) Foreign Application Priority Data

Jun. 3, 2003 (DK) .................. 2003 00819
Jan. 19, 2004 (DK) .................. 2004 00075

(51) Int. Cl.
*A61K 38/26* (2006.01)
(52) U.S. Cl. .............. 514/2; 530/308; 530/412
(58) Field of Classification Search ............ 514/2; 530/308, 412
See application file for complete search history.

(56) References Cited

U.S. PATENT DOCUMENTS

| 5,272,135 A | * | 12/1993 | Takruri | 514/12 |
| 5,705,483 A | | 1/1998 | Galloway et al. | |
| 6,184,201 B1 | * | 2/2001 | Drucker et al. | 514/12 |
| 6,586,399 B1 | * | 7/2003 | Drucker | 514/12 |
| 7,022,674 B2 | | 4/2006 | DeFelippis et al. | |
| 7,049,284 B2 | * | 5/2006 | Drucker | 514/2 |
| 7,056,886 B2 | * | 6/2006 | Isaacs | 514/12 |
| 7,112,567 B2 | * | 9/2006 | Bridon et al. | 514/12 |
| 2003/0060412 A1 | | 3/2003 | Prouty, Jr. et al. | |
| 2003/0069182 A1 | | 4/2003 | Rinella | |

FOREIGN PATENT DOCUMENTS

| WO | 99/29336 | 12/1998 |
| WO | 99/30731 | 12/1998 |
| WO | 00/37098 | 12/1999 |
| WO | WO 01/49314 | 7/2001 |
| WO | 02/47715 | 12/2001 |
| WO | 02/48183 | 12/2001 |
| WO | 03/002136 | 6/2002 |
| WO | 03/020201 | 8/2002 |

OTHER PUBLICATIONS

Senderoff—J Pharm Sci—1998—vol. 87—pp. 183-189.
Malendowicz, L.K. et al., "Preproglucagon derived peptides and thyrotropin (TSH) secretion in the fat: Robust and sustained lowering of blood TSH levels in exendin-4 injected animals", International Journal of Molecular Medicine, vol. 10, pp. 327-331 (2002).

* cited by examiner

*Primary Examiner*—David Lukton
(74) *Attorney, Agent, or Firm*—Shelby J. Walker

(57) ABSTRACT

A method is disclosed for increasing the shelf-life of a pharmaceutical composition for parenteral administration comprising a glucagon-like peptide which is prepared from a peptide product that has been subjected to treatment at a pH above neutral pH.

39 Claims, No Drawings

```
                    SEQUENCE LISTING

<160> NUMBER OF SEQ ID NOS: 6

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 31
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 33
<212> TYPE: PRT
<213> ORGANISM: Homo sapiens

<400> SEQUENCE: 3

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 4
<211> LENGTH: 39
<212> TYPE: PRT
<213> ORGANISM: Homo sapiens

<400> SEQUENCE: 4

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 5
<211> LENGTH: 39
<212> TYPE: PRT
<213> ORGANISM: Homo sapiens

<400> SEQUENCE: 5

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 6
<211> LENGTH: 37
<212> TYPE: PRT
<213> ORGANISM: Homo sapiens

<400> SEQUENCE: 6

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asp Thr Lys Arg Asn
            20                  25                  30

Lys Asn Asn Ile Ala
        35
```

STABILIZED PHARMACEUTICAL PEPTIDE COMPOSITIONS

This application is a continuation of PCT/DK04/00380, filed Jun. 3, 2004, which claims priority to applications PA 2004/00075, filed Jan. 19, 2004 and PA 2003/00819, filed Jun. 3, 2003.

FIELD OF THE INVENTION

The present invention relates to the field of pharmaceutical compositions. More specifically the invention pertains to methods for preparing stable pharmaceutical compositions which are prepared from a bulk peptide product that has been subjected to treatment at pH above neutral pH.

BACKGROUND OF THE INVENTION

Therapeutic peptides are widely used in medical practise. Pharmaceutical compositions of such therapeutic peptides are required to have a shelf life of several years in order to be suitable for common use. However, peptide compositions are inherently unstable due to sensitivity towards chemical and physical degradation. Chemical degradation involves change of covalent bonds, such as oxidation, hydrolysis, racemization or crosslinking. Physical degradation involves conformational changes relative to the native structure of the peptide, i.e. secondary and tertiary structure, such as aggregation, precipitation or adsorption to surfaces.

Glucagon has been used for decades in medical practise within diabetes and several glucagon-like peptides are being developed for various therapeutic indications. The preproglucagon gene encodes glucagon as well as glucagon-like peptide 1 (GLP-1) and glucagon-like peptide 2 (GLP-2). GLP-1 analogs and derivatives as well as the homologous lizard peptide, exendin-4, are being developed for the treatment of hyperglycemia within type 2 diabetes. GLP-2 are potentially useful in the treatment of gastrointestinal diseases. However, all these peptides encompassing 29-39 amino acids have a high degree of homology and they share a number of properties, notably their tendency to aggregate and formation of insoluble fibrils. This property seems to encompass a transition from a predominant alpha-helix conformation to beta-sheets (Blundell T. L. (1983) The conformation of glucagon. In: Lefébvre P. J. (Ed) Glucagon I. Springer Verlag, pp 37-55, Senderoff R. I. et al., J. Pharm. Sci. 87 (1998)183-189, WO 01/55213). Aggregation of the glucagon-like peptides are mainly seen when solutions of the peptides are stirred or shaken, at the interface between solution and gas phase (air), and at contact with hydrophobic surfaces such as Teflon®.

Thus, various excipients must often be added to pharmaceutical compositions of the glucagon-like peptides in order to improve their stability. Shelf life of liquid parenteral formulations of these peptides must be at least a year, preferably longer. The in-use period where the product may be transported and shaken daily at ambient temperature preferably should be several weeks. Thus, there is a need for pharmaceutical compositions of glucagon-like peptides which have improved stability.

SUMMARY OF THE INVENTION

The present invention relates to the unexpected finding that bulk peptide products which have been treated at a pH above 8.0 increased the stability of the pharmaceutical compositions prepared from these bulk peptide products.

The present invention therefore relates to methods for increasing the shelf-life of a pharmaceutical composition for parenteral administration comprising a glucagon-like peptide which is prepared from a glucagon-like peptide product that has been subjected to treatment at a pH above neutral pH, to pharmaceutical compositions produced by such methods and to the use of such compositions in methods of treatment.

DEFINITIONS

The following is a detailed definition of the terms used in the specification.

The term "effective amount" as used herein means a dosage which is sufficient to be effective for the treatment of the patient compared with no treatment.

The term "reconstituted" as used herein referring to a pharmaceutical composition means an aqueous composition which has been formed by the addition of water or an appropriate aqueous solution to a solid material comprising the active pharmaceutical ingredient. Pharmaceutical compositions for reconstitution are applied where a liquid composition with acceptable shelf-life cannot be produced. An example of a reconstituted pharmaceutical composition is the solution which results when adding water or an appropriate aqueous solution to a freeze dried composition. The solution is often for parenteral administration and thus water for injection or any other appropriate solvent are used for reconstituting the solid material.

The term "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The term "glucagon-like peptide" as used herein refers to the homologous peptides derived from the preproglucagon gene, exendins and analogues and derivatives thereof. The peptides derived from the preproglucagon gene is glucagon, glucagon-like peptide 1 (GLP-1), glucagon-like peptide 2 (GLP-2) and oxynthomodulin (OXM). The exendins which are found in the Gila monster are homologous to GLP-1 and also exert an insulinotropic effect. Examples of exendins are exendin-4 and exendin-3.

The glucagon-like peptides have the following sequences:

|  | 1 | 5 | 10 | 15 | 20 | 25 | 30 | 35 |
|---|---|---|---|---|---|---|---|---|
| Glucagon | HSQGT | FTSDY | SKYLD | SRRAQ | DFVQW | LMNT-NH2 | | |
| GLP-1 | HAEGT | FTSDV | SSYLE | GQAAK | EFIAW | LVKGR | G | |
| GLP-2 | HADGS | FSDEM | NTILD | NLAAR | DFINW | LIQTK | ITD | |
| Exendin-4 | HGEGT | FTSDL | SKQME | EEAVR | LFIEW | LKNGG | PSSGA | PPPS-NH2 |

```
-continued

Exendin-3  HSDGT  FTSDL  SKQME  EEAVR  LFIEW  LKNGG    PSSGA  PPPS-NH2

OXM           HSQGT  FTSDY  SKYLD  SRRAQ  DFVQW  LMDTK    RNKNN  IA
```

The term "analogue" as used herein referring to a peptide means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide. Two different and simple systems are often used to describe analogues : For example Arg$^{34}$-GLP-1(7-37) or K34R-GLP-1(7-37) designates a GLP-1 analogue wherein amino acid residues at position 1-6 have been deleted, and the naturally occuring lysine at position 34 has been substituted with arginine (standard single letter abbreviation for amino acids used according to IUPAC-IUB nomenclature).

The term "derivative" as used herein in relation to a parent peptide means a chemically modified parent protein or an analogue thereof, wherein at least one substituent is not present in the parent protein or an analogue thereof, i.e. a parent protein which has been covalently modified. Typical modifications are amides, carbohydrates, alkyl groups, acyl groups, esters, pegylations and the like. An examples of a derivative of GLP-1(7-37) is Arg$^{34}$, Lys$^{26}$(N$^\epsilon$-(γ-Glu(N$^\alpha$-hexadecanoyl)))-GLP-1(7-37).

The term "GLP-1 peptide" as used herein means GLP-1(7-37), a GLP-1 analogue, a GLP-1 derivative or a derivative of a GLP-1 analogue.

The term "GLP-2 peptide" as used herein means GLP-2(1-33), a GLP-2 analogue, a GLP-2 derivative or a derivative of a GLP-2 analogue.

The term "exendin-4 peptide" as used herein means exendin-4(1-39), an exendin-4 analogue, an exendin-4 derivative or a derivative of an exendin-4 analogue.

The term "stable exendin-4 compound" as used herein means a chemically modified exendin-4(1-39), i.e. an analogue or a derivative which exhibits an in vivo plasma elimination half-life of at least 10 hours in man, as determined by the following method. The method for determination of plasma elimination half-life of an exendin-4 compound in man is: The compound is dissolved in an isotonic buffer, pH 7.4, PBS or any other suitable buffer. The dose is injected peripherally, preferably in the abdominal or upper thigh. Blood samples for determination of active compound are taken at frequent intervals, and for a sufficient duration to cover the terminal elimination part (e.g. Pre-dose, 1, 2, 3, 4, 5, 6, 7, 8, 10, 12, 24 (day 2), 36 (day 2), 48 (day 3), 60 (day 3), 72 (day 4) and 84 (day 4) hours post dose). Determination of the concentration of active compound is performed as described in Wilken et al., Diabetologia 43(51):A143, 2000. Derived pharmacokinetic parameteres are calculated from the concentration-time data for each individual subject by use of non-compartmental methods, using the commercially available software WinNonlin Version 2.1 (Pharsight, Cary, N.C., USA). The terminal elimination rate constant is estimated by log-linear regression on the terminal log-linear part of the concentration-time curve, and used for calculating the elimination half-life.

The term "DPP-IV protected exendin-4 compound" as used herein means an exendin-4 compound which has been chemically modified to render said compound resistant to the plasma peptidase dipeptidyl aminopeptidase-4 (DPP-IV).

The term "immunomodulated exendin-4 compound" as used herein means an exendin-4 compound which is an analogue or a derivative of exendin-4(1-39) having a reduced immune response in humans as compared to exendin-4(1-39). The method for assessing the immune response is to measure the concentration of antibodies reactive to the exendin-4 compound after 4 weeks of treatment of the patient.

The term "bulk product" or "bulk peptide product" as used herein means the purified peptide product which is to be used for the manufacture of a pharmaceutical composition. Thus, the bulk product is normally obtained as the product from the final purification, drying or conditioning step. The bulk product may be crystals, precipitate, solution or suspension. The bulk product is also known in the art as the drug substance.

The term "isoelectric point" as used herein means the pH value where the overall net charge of a macromolecule such as a peptide is zero. In peptides there may be many charged groups, and at the isoelectric point the sum of all these charges is zero, i.e. the number of negative charges balances the number of positive charges. At a pH above the isoelectric point the overall net charge of the peptide will be negative, whereas at pH values below the isoelectric point the overall net charge of the peptide will be positive. The isoelectric point of a peptide may be determined by isoelectric focusing or it may be estimated from the sequence of the peptide by computational algorithms known in the art.

DESCRIPTION OF THE INVENTION

In one aspect the present invention relates to a method for increasing the shelf-life of a pharmaceutical composition which comprises a glucagon-like peptide, a pharmaceutically acceptable buffer and a pharmaceutically acceptable preservative, characterized in that said pharmaceutical composition is prepared from a bulk peptide product which has been subjected to treatment at a pH in the range from 8.1 to 9.6.

In another aspect the present invention relates to a method for increasing the shelf-life of a pharmaceutical composition which comprises a glucagon-like peptide and a pharmaceutically acceptable preservative, characterized in that said pharmaceutical composition is prepared from a bulk peptide which has been subjected to treatment at a pH in the range from 8.1 to 9.6.

In another aspect the present invention relates to a method for increasing the shelf-life of a pharmaceutical composition which comprises a peptide, a pharmaceutically acceptable buffer and a pharmaceutically acceptable preservative, characterized in that said pharmaceutical composition is prepared from a bulk peptide product which has been subjected to treatment at a pH in the range from 8.1 to 9.6.

In another aspect the present invention relates to a method for increasing the shelf-life of a pharmaceutical composition which comprises a peptide and a pharmaceutically acceptable preservative, characterized in that said pharmaceutical composition is prepared from a bulk peptide which has been subjected to treatment at a pH in the range from 8.1 to 9.6.

In another aspect the present invention relates to a method for increasing the shelf-life of a pharmaceutical composition which comprises a glucagon-like peptide, a pharmaceutically acceptable buffer and a pharmaceutically acceptable preservative, characterized in that said pharmaceutical composition is prepared from a bulk peptide product which has been subjected to treatment at a pH in the range from 8.5 to 9.6.

In one aspect the present invention relates to a method for increasing the shelf-life of a pharmaceutical composition which comprises a glucagon-like peptide, a pharmaceutically acceptable buffer and a pharmaceutically acceptable preservative, characterized in that said pharmaceutical composition is prepared from a bulk peptide product which has been subjected to treatment at a pH in the range from 9.0 to 9.6.

In one aspect the present invention relates to a method for increasing the shelf-life of a pharmaceutical composition which comprises a glucagon-like peptide, a pharmaceutically acceptable buffer and a pharmaceutically acceptable preservative, characterized in that said pharmaceutical composition is prepared from a bulk peptide product which has been subjected to treatment at a pH in the range from 8.1 to 11.5.

In one embodiment the bulk peptide product has been subjected to a pH in the range from 8.1 to 10.0.

In another embodiment the bulk peptide product has been subjected to a pH in the range from 8.5 to 11.5.

In another embodiment the bulk peptide product has been subjected to a pH in the range from 8.5 to 10.0.

In another embodiment of the invention the bulk peptide product has been subjected to treatment at a pH in the specified range for a period from about 1 minute to about 12 hours, and at a temperature higher than the nucleation temperature (either as heterogeneous or homogeneous nucleation) of the bulk peptide to about 25° C.

In another embodiment of the invention the bulk peptide product has been subjected to treatment at a pH in the specified range for a period from 1 minute to 30 minutes, and at a temperature from about 5° C. to about 25° C.

It is to be understood that the invention may be realized through various combinations of pH values, temperature and time. These three variables may be combined within the above mentioned ranges. However, whereas one or two of the variables may suitably be chosen at the high end of the ranges, the remaining one or two variables are typically lower. For instance, if a high pH value such as pH 10 is used it is preferably combined with a lower temperature such as about 5-10° C. and/or a short time such as less than about 1 minute to about 6 hours. Useful combinations of variables are: pH 10.0 at 5° C. for about 3 hours, pH 10.0 at 15° C. for about 1 hour, or pH 11.0 at 5° C. for about 1 hours.

The growth of ice crystals, whether as a single crystal or as a polycrystal, is the initial nucleation process, only ice is produced with the freezing of water or a aqueous solution at low pressures, both on slow and rapid freezing. The nucleation of solutions may take place in two ways, depending on the concentration of the solute and the temperature. If a saturated solution is cooled, then it may become not only supercooled with respect to the ice phase, but also supersaturated with respect to the solute. In absence of appropriate freezing nuclei, the solution may supercool. Thus the temperature used during the treatment of the peptide at higher pH is to be kept above the nucleation temperature of the peptide at the prevailing conditions. The nucleation temperature is known to the person skilled in the art, and it may routinely be determined for the relevant peptide by experiments at different temperatures.

In one embodiment the pharmaceutical composition is a solution.

In another embodiment the pharmaceutical composition is a suspension.

In another embodiment the pharmaceutical composition is a solid, e.g. a freeze-dried formulation whereto the physician or the patient adds the solvent prior to use. The solvent used for reconstitution may be water for injection or another suitable solvent.

In another embodiment the bulk peptide product is prepared by freeze drying a solution or suspension of said glucagon-like peptide at said pH.

In another embodiment the bulk peptide product is treated at said pH during the manufacture of said pharmaceutical composition.

In another embodiment the bulk peptide product is treated at said pH after the final purification step in the manufacturing process.

In another embodiment the bulk peptide product is treated at said pH before being mixed with said pharmaceutically acceptable buffer.

In another embodiment the pH of the pharmaceutical composition is lower than the pH at which the solution or suspension of the bulk peptide is treated.

In another embodiment the pH of the pharmaceutical composition is at least 0.8 pH units lower than the pH at which the solution or suspension of the bulk peptide is treated.

In another embodiment the pH of said pharmaceutical composition is at least 1.5 pH units lower than the pH at which the solution or suspension of the bulk peptide is treated.

Pharmaceutical compositions comprising a glucagon-like peptide according to the present invention may be administered parenterally to patients in need of such treatment. Parenteral administration may be performed by subcutaneous injection, intramuscular injection, or intravenous injection by means of a syringe, optionally a pen-like syringe. Alternative administration can be performed by infusion, e.g. by use of an infusion pump.

In one embodiment the pH of said pharmaceutical composition or a reconstituted solution of said pharmaceutical composition is from pH 7.0 to pH 8.0, preferably from pH 7.2 to pH 7.8. In another embodiment the pH of said pharmaceutical composition or a reconstituted solution of said pharmaceutical composition is from pH 7.2 to pH 7.6. In another embodiment the pH of said pharmaceutical composition or a reconstituted solution of said pharmaceutical composition is from pH 7.4 to pH 7.8.

In another embodiment the isoelectric point of said glucagon-like peptide is from 3.0 to 7.0, preferably from 4.0 to 6.0.

In one embodiment said glucagon-like peptide is glucagon, a glucagon analogue or a derivative thereof.

In another embodiment said glucagon-like peptide is oxynthomodulin.

In one embodiment said glucagon-like peptide is GLP-1, a GLP-1 analogue, a derivative of GLP-1 or a derivative of a GLP-1 analogue.

In another embodiment said GLP-1 analogue is selected from the group consisting of $Gly^8$-GLP-1(7-36)-amide, $Gly^8$-GLP-1(7-37), $Val^8$-GLP-1(7-36)-amide, $Val^8$-GLP-1(7-37), $Val^8Asp^{22}$-GLP-1(7-36)-amide, $Val^8Asp^{22}$-GLP-1(7-37), $Val^8Glu^{22}$-GLP-1(7-36)-amide, $Val^8Glu^{22}$-GLP-1(7-37), $Val^8Lys^{22}$-GLP-1(7-36)-amide, $Val^8Lys^{22}$-GLP-1(7-37), $Val^8Arg^{22}$-GLP-1(7-36)-amide, $Val^8Arg^{22}$-GLP-1(7-37), $Val^8His^{22}$-GLP-1(7-36)-amide, $Val^8His^{22}$-GLP-1(7-37), $Val^8Trp^{19}Glu^{22}$-GLP-1(7-37), $Val^8Glu^{22}Val^{25}$-GLP-1(7-37), $Val^8Tyr^{16}Glu^{22}$-GLP-1(7-37), $Val^8Trp^{16}Glu^{22}$-GLP-1(7-37), $Val^8Leu^{16}Glu^{22}$-GLP-1(7-37), $Val^8Tyr^{18}Glu^{22}$-GLP-1

(7-37), Val$^8$Glu$^{22}$-His$^{37}$-1(7-37), Val$^8$Glu$^{22}$Ile$^{33}$-GLP-1(7-37), Val$^8$Trp$^{16}$Glu$^{22}$Val$^{25}$Ile$^{33}$-GLP-1(7-37), Val$^8$Trp$^{16}$Glu$^{22}$Ile$^{33}$-GLP-1(7-37), Val$^8$Glu$^{22}$Val$^{25}$Ile$^{33}$-GLP-1(7-37), Val$^8$Trp$^{16}$Glu$^{22}$Val$^{25}$-GLP-1(7-37), and analogues thereof.

In another embodiment said derivative of a GLP-1 analogue is Arg$^{34}$, Lys$^{26}$(N$^\epsilon$-(γ-Glu(N$^\alpha$-hexadecanoyl)))-GLP-1 (7-37).

Methods for the preparation of GLP-1, analogues thereof as well as GLP-1 derivatives can be found in e.g. WO 99/43706, WO 00/55119, WO 00/34331 and WO 03/18516.

In another embodiment said solution or suspension of the bulk peptide product is subjected to treatment at a pH of 9.5, and the pH of said pharmaceutical composition is 7.4.

In another embodiment the glucagon-like peptide is a GLP-1 peptide and the pharmaceutical composition or a reconstituted composition thereof has a glucacon-like peptide concentration from 0.1 mg/mL to 50 mg/mL, from 0.1 mg/mL to 25 mg/mL, from 1 mg/mL to 25 mg/mL, from 1 mg/mL to 10 mg/mL, or from 3 mg/mL to 8 mg/mL.

In one embodiment the glucagon-like peptide is GLP-2, a GLP-2 analogue, a derivative of GLP-2 or a derivative of a GLP-2 analogue.

In another embodiment the derivative of GLP-2 or a derivative of a GLP-2 analogue has a lysine residue, such as one lysine, wherein a lipophilic substituent optionally via a spacer is attached to the epsilon amino group of said lysine.

Methods for the preparation of GLP-2, analogs thereof as well as GLP-2 derivatives can be found in e.g. WO 99/43361 and WO 00/55119.

In another embodiment the glucagon-like peptide is a GLP-2 peptide and the pharmaceutical composition or a reconstituted composition thereof has a glucagon-like peptide concentration from 0.1 mg/mL to 100 mg/mL, from 0.1 mg/mL to 25 mg/mL, or from 1 mg/mL to 25 mg/mL.

In one embodiment the glucagon-like peptide is exendin-4, an exendin-4 analogue, a derivative of exendin-4, or a derivative of an exendin-4 analogue.

In another embodiment the glucagon-like peptide is exendin-4. In another embodiment the glucagon-like peptide is a stable exendin-4. In another embodiment the glucagon-like peptide is a DPP-IV protected exendin-4. In another embodiment the glucagon-like peptide is an immuno-modulated exendin-4. In another embodiment the glucagon-like peptide is ZP-10 ([Ser$^{38}$Lys$^{39}$]Exendin-4(1-39)LysLysLysLysLys-amide).

Methods for the preparation of exendin-4, analogues thereof as well as exendin-4 derivatives can be found in e.g. WO 99/43708, WO 00/41546 and WO 00/55119.

In another embodiment the glucagon-like peptide is an exendin-4 peptide and the pharmaceutical composition or a reconstituted composition thereof has a concentration of glucagon-like peptide from 5 μg/mL to 10 mg/mL, from 5 μg/mL to 5 mg/mL, from 5 μg/mL to 5 mg/mL, from 0.1 mg/mL to 3 mg/mL, or from 0.2 mg/mL to 1 mg/mL.

Buffers suitable for use in pharmaceutical compositions are known to those skilled in the art and include, but are not limited to, orhto-phosphate, TRIS, glycine, N-glycylglycine, citrate sodium acetate, sodium carbonate, glycylglycine, histidine, lysine, arginine, sodium phosphate, and sodium citrate or mixtures thereof. In one embodiment the pharmaceutical composition comprises a buffer which is Tris. In another embodiment the pharmaceutical composition comprises a buffer which is Bicine.

Preservatives for use in pharmaceutical compositions are known to those skilled in the art and include, but are not limited to, phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof.

In one embodiment the pharmaceutical composition comprises an isotonicity agent.

In another embodiment the pharmaceutical composition comprises an isotonicity agent which is sodium chloride, xylitol, mannitol, sorbitol, glycerol, glucose, maltose, sucrose, L-glycine, L-histidine, arginine, lysine, isoleucine, aspartic acid, tryptophan, threonine, dimethyl sulphone, polyethyleneglycol, propylene glycol or mixtures thereof.

In another embodiment of the present invention the pharmaceutical composition further comprises a stabilizer.

In a further embodiment of the invention the formulation further comprises a stabilizer selected from the group of high molecular weight polymers or low molecular compounds.

In a further embodiment of the invention the stabilizer is selected from polyethylene glycol (e.g. PEG 3350), polyvinylalcohol (PVA), polyvinylpyrrolidone, carboxymethylcellulose, different salts (e.g. sodium chloride), L-glycine, L-histidine, imidazole, arginine, lysine, isoleucine, aspartic acid, tryptophan, threonine and mixtures thereof. Each one of these specific stabilizers constitutes an alternative embodiment of the invention. In a preferred embodiment of the invention the stabilizer is selected from the group consisting of L-histidine, imidazole and arginine.

In another embodiment of the present invention the stabilizer is selected from the group consisting of PEG 3350, polyvinylalcohol, polyvinylpyrrolidone, carboxy-methylcellulose, sodium chloride, L-glycine, L-histidine, imidazole, L-arginine, L-lysine, L-isoleucine, L-aspartic acid, L-tryptophan, L-threonine and mixtures thereof.

In a further embodiment of the invention the formulation further comprises a chelating agent. In a further embodiment of the invention the chelating agent is selected from salts of ethlenediaminetetraacetic acid (EDTA), citric acid, and aspartic acid, and mixtures thereof. Each one of these specific chelating agents constitutes an alternative embodiment of the invention.

In another embodiment of the present invention the pharmaceutical composition further comprises a surfactant. In a further embodiment of the invention the surfactant is selected from a detergent, ethoxylated castor oil, polyglycolyzed glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g. Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N, N-dimethyl-3-ammonio-1-propanesulfonate, anionic (alkyl-aryl-sulphonates) monovalent surfactants, palmitoyl lyso-phosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the postively charged DODAC, DOTMA, DCP, BISHOP, lysophosphatidylserine and lyso-phosphatidylthreonine, zwitterionic surfactants (e.g. N-alkyl-N,N-dimethylammonio-1-propanesulfonates, 3-cholamido-1-propyldimethylammonio-1-propanesulfonate, dodecylphosphocholine, myristoyl lysophosphatidylcholine, hen egg lysolecithin), cationic surfactants (quarternary ammonium bases) (e.g. cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives-(e.g. sodium tauro-dihydrofusidate etc.), long-chain fatty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, or the surfactant may be selected from the group of imidazoline derivatives, or mixtures thereof. Each one of these specific surfactants constitutes an alternative embodiment of the invention.

The use of excipients such as preservatives, isotonic agents and surfactants in pharmaceutical compositions is well-known to the skilled person. For convenience reference is made to Remington: *The Science and Practice of Pharmacy*, 19$^{th}$ edition, 1995.

In a further aspect the present invention relates to a pharmaceutical composition which comprises a glucagon-like peptide, a pharmaceutically acceptable buffer and a pharmaceutically acceptable preservative, characterized in that said pharmaceutical composition is prepared by a method according to the present invention.

In a further aspect the present invention relates to a pharmaceutical composition having a pH between about 7.2 to about 7.8, said composition comprising a glucagon-like peptide and at least one pharmaceutically acceptable excipient, wherein said composition is shelf stable as measured by a less than two fold increase of fluorescence in a Thioflavin T test of the glucagon-like peptide contained in said composition after storage of the composition for one month at 37° C.

In a further aspect the present invention relates to a pharmaceutical composition which comprises a peptide, a pharmaceutically acceptable buffer and a pharmaceutically acceptable preservative, characterized in that said pharmaceutical composition is prepared by a method according to the present invention.

In a further aspect the present invention relates to a method for treatment of hyperglycemia comprising parenteral administration of an effective amount of the pharmaceutical composition according to the present invention.

The parent glucagon-like peptide can be produced by peptide synthesis, e.g. solid phase peptide synthesis using t-Boc or F-Moc chemistry or other well established techniques. The parent glucagon-like peptide can also be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the parent peptide may suitably be of genomic or cDNA origin, for instance obtained by preparing a genomic or cDNA library and screening for DNA sequences coding for all or part of the peptide by hybridisation using synthetic oligonucleotide probes in accordance with standard techniques (see, for example, Sambrook, J, Fritsch, E F and Maniatis, T, Molecular Cloning: A Laboratory Manual, Cold Spring Harbor Laboratory Press, New York, 1989). The DNA sequence encoding the peptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. The DNA sequence may also be prepared by polymerase chain reaction using specific primers, for instance as described in U.S. Pat. No. 4,683,202 or Saiki et al., Science 239 (1988), 487-491. The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well known in the art, cf. for instance Sambrook et al., supra.

The DNA sequence encoding the peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a parent peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the present peptide, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are, without limitation, *E. coli, Saccharomyces cerevisiae*, or mammalian BHK or CHO cell lines.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

In the following "Compound 1" is intended to mean: $Arg^{34}$, $Lys^{26}$ ($N^{\epsilon}$-($\gamma$-Glu($N^{\alpha}$-hexadecanoyl)))-GLP-1(7-37).

Before freeze drying the solution or suspension of the peptide it has been adjusted to the aimed pH. After freeze drying pharmaceutical formulations were prepared according to General procedure 1 and 2.

General Procedure 1

Preservative, isotonic agent and buffer were dissolved in water and pH adjusted to 7.4. Hereafter the freeze dried peptide was dissolved while stirring slowly. The pH was adjusted to 7.4 using Sodium Hydroxide and/or Hydrochloric Acid. Finally, the formulation was filtered through a 0.22 μm filter.

General Procedure 2

Preservative, isotonic agent and buffer were dissolved in water and pH adjusted to 7.4. The peptide was dissolved in water while stirring slowly. The two solutions were mixed and pH adjusted to 7.4 using Sodium Hydroxide and/or Hydrochloric acid. Finally, the formulation was filtered through a 0.22 μm filter.

Another way to make a stable pharmaceutical formulation is to raise pH above neutral pH (>8) in the solution containing the drug substance. The pharmaceutical formulation is prepared as described in general procedure 3.

General Procedure 3

Preservative, isotonic agent and buffer were dissolved in water and pH adjusted to 7.4 or lower. Compound 1 was dissolved in water while stirring slowly and pH is adjusted to 11.5 by the addition of Sodium Hydroxide. After approx. 5 min the two solutions were mixed and pH adjusted to 7.4 using Sodium Hydroxide and/or Hydrochloric acid. Finally, the formulation was filtered through a 0.22 μm filter.

Physical stability of the formulations is evaluated by means of the Thioflavin T-test. The physical stability of the different formulations is characterized by their tendency to form fibrils. A method to determine the presence of fibrils is the Thioflavin T-test. The histological thiazole dye Thioflavin T (ThT) is used as an indicator of amyloid fibril formation. The method is based on the fluorescent characteristics of ThT. In the presence of amyloid fibrils, the fluorescense of ThT exhibits an excitation maximum at 450 nm and enhanced emission at 482 nm. The ThT fluorescence intensity has been shown to be linear with the increase in amyloid fibril concentration. The physical stability of the formulations is evaluated by the ThT-test after storage of the formulation is top filled glass cartridges for various time periods.

Results from Pharmaceutical Formulation Manufactured with Drug Substance Adjusted to a pH Above Neutral pH (>8) Before Freeze Drying The results from ThT-test at start (t=0) and after 1 months storage at 37° C. can be seen in Table 1.

TABLE 1

Results from ThT-test (fluorescence units) after 1 week or 1 month of accelerated stability testing.

| pH of Compound 1 before freeze drying | Concentration of Compound 1 in pharmaceutical formulation | pH of pharmaceutical formulation | Fluorescence units after storage at 37° C. | | |
|---|---|---|---|---|---|
| | | | T = 0 week | T = 1 week | T = 1 month |
| 8.0 | 3 mg/ml | 7.4 | 6 | Not determined | 28 |
| 9.5 | 3 mg/ml | 7.4 | 6 | Not determined | 7 |
| 11.5 | 3 mg/ml | 7.4 | 6 | Not determined | 7 |
| 8.0 | 6.25 mg/ml | 7.4 | 13 | 20 | 37 |
| 9.5 | 6.25 mg/ml | 7.4 | 14 | 13 | 13 |
| 11.5 | 6.25 mg/ml | 7.4 | 14 | 13 | 14 |

It is seen that the pharmaceutical formulations manufactured with Compound 1 adjusted to pH 9.5 and 11.5 before freeze drying is more physically stable after 1 week and 1 months storage at 37° C. (as no increase in ThT is seen) compared to the pharmaceutical formulation manufactured with Compound 1 adjusted to pH 8.0 before freeze drying (where an increase in ThT is seen).

Results of Pharmaceutical Formulation Manufactured by Raising pH Above Neutral pH (>8) in the Solution Containing the Drug Substance.

TABLE 2

| pH of solution containing the drug substance | Concentration of Compound 1 in pharmaceutical formulation | pH of pharmaceutical formulation | Fluorescence units after storage at 37° C. | | |
|---|---|---|---|---|---|
| | | | T = 0 week | T = 1 week | T = 1 month |
| 8.0 | 6.25 mg/ml | 7.4 | 14 | 20 | 41 |
| 11.5 | 6.25 mg/ml | 7.4 | 13 | 12 | 13 |

Results from ThT-test (fluorescence units) after 1 month of accelerated stability testing.

It is seen that the pharmaceutical formulation manufactured by raising pH above neutral pH (>8) in the solution containing the drug substance is physically stable after 1 month at 37° C. (as no increase in ThT is seen) compared to the pharmaceutical formulation manufactured without the increase of pH to above neutral pH (>8).

The invention claimed is:

1. A method for increasing the shelf-life of a pharmaceutical composition comprising a glucagon-like peptide, said method comprising the steps of: a) providing a solution or suspension of bulk glucagon-like peptide product; b) subjecting said bulk glucagon-like peptide product to a pH in the range from 8.5 to 9.6; and c) preparing a pharmaceutical composition comprising the glucagon-like peptide product of step b), wherein said pharmaceutical composition also comprises a pharmaceutically acceptable buffer and a pharmaceutically acceptable preservative, and wherein the pH of said pharmaceutical composition is at least 0.8 pH units lower than the pH at which the solution or suspension of the bulk glucagon-like peptide product has been subjected.

2. The method according to claim 1, wherein said pH is in the range from 9.0 to 9.6.

3. The method according to claim 1, wherein said bulk peptide product has been subjected to said pH range for a time period from 10 minutes to 12 hours and at a temperature from about 5° C. to about 25° C.

4. The method according to claim 1, wherein said bulk peptide product has been subjected to said pH range for a time period from 1 minute to 30 minutes, and at a temperature from about 5° C. to about 25° C.

5. The method according to claim 1, wherein said pharmaceutical composition is a solution.

6. The method according to claim 1, wherein said pharmaceutical composition is a suspension.

7. The method according to claim 1, further comprising step d) freeze drying said pharmaceutical composition to form a solid.

8. The method according to claim 7, wherein said pharmaceutical composition is to be reconstituted with water or another suitable solvent for injection.

9. The method according to claim 1, wherein said bulk peptide product is prepared by freeze drying a solution or suspension of said glucagon-like peptide at said pH of step (b).

10. The method according to claim 1, wherein said bulk peptide product is subjected to said pH range during the preparation of said pharmaceutical composition.

11. The method according to claim 1, wherein said bulk peptide product is subjected to said pH range before being mixed with said pharmaceutically acceptable buffer.

12. The method according to claim 1, wherein the pH of said pharmaceutical composition is at least 1.5 pH units lower than the pH at which the solution or suspension of the bulk peptide is subjected.

13. The method according to claim 1, wherein the pharmaceutical composition is suitable for parenteral administration.

14. The method according to claim 1, wherein the pH of said pharmaceutical composition or a reconstituted solution of said pharmaceutical composition is from pH 7.0 to pH 8.0.

15. The method according to claim 1, wherein the pH of said pharmaceutical composition or a reconstituted solution of said pharmaceutical composition is from pH 7.2 to pH 7.8.

16. The method according to claim 1, wherein the isoelectric point of said glucagon-like peptide is from 3.0 to 7.0.

17. The method according to claim 1, wherein the isoelectric point of said glucagon-like peptide is from 4.0 to 6.0.

18. The method according to claim 1, wherein said glucagon-like peptide is glucagon, a glucagon analogue or a derivative thereof.

19. The method according to claim 1, wherein said glucagon-like peptide is glucagon-like peptide 1 (GLP-1), a GLP-1 analogue, a derivative of GLP-1 or a derivative of a GLP-1 analogue.

20. The method according to claim 19, wherein said GLP-1 analogue is selected from the group consisting of $Gly^8$-GLP-1(7-36)-amide, $Gly^8$-GLP-1(7-37), $Val^8$-GLP-1(7-36)-amide, $Val^8$-GLP-1(7-37), $Val^8Asp^{22}$-GLP-1(7-36)-amide, $Val^8Asp^{22}$-GLP-1(7-37), $Val8Glu^{22}$-GLP-1(7-36)-amide, $Val^8Glu^{22}$-GLP-1(7-37), $Val^8Lys^{22}$-GLP-1(7-36)-amide, $Val^8Lys^{22}$-GLP-1(7-37), $Val^8Arg^{22}$-GLP-1(7-36)-amide, $Val^8Arg^{22}$-GLP-1(7-37), $Val^8His^{22}$-GLP-1(7-36)-amide, $Val^8His^{22}$-GLP-1(7-37), $Val^8Trp^{19}Glu^{22}$-GLP-1(7-37), $Val^8Glu^{22}Val^{25}$-GLP-1(7-37), $Val^8Tyr^{16}Glu^{22}$-GLP-1(7-37), $Val^8Trp^{16}Glu^{22}$-GLP-1(7-37), $Val^8Leu^{16}Glu^{22}$-GLP-1(7-37), $Val^8Tyr^{18}Glu^{22}$-GLP-1(7-37), $Val^8Glu^{22}His^{37}$-GLP-1(7-37), $Val^8Glu^{22}Ile^{33}$-GLP-1(7-37), $Val^8Trp^{16}Glu^{22}Val^{25}$-GLP-1(7-37), $Val^8Trp^{16}Glu^{22}Ile^{33}$-GLP-1(7-37), $Val^8Glu^{22}Val^{25}Ile^{33}$-GLP-1(7-37), $Val^8Trp^{16}Glu^{22}Val^{25}$-GLP-1(7-37), and analogues thereof.

21. The method according to claim 19, wherein said derivative of a GLP-1 analogue is $Arg^{34}$, $Lys^{26}(N^\epsilon-(\gamma Glu(N^\alpha-hexadecanoyl)))$-GLP-1-(7-37).

22. The method according to claim 1, wherein said solution or suspension of the bulk peptide product is subjected to treatment at a pH of 9.5, and the pH of said pharmaceutical composition is 7.4.

23. The method according to claim 18, wherein the concentration of said glucagon-like peptide in the pharmaceutical composition is from 0.1 mg/mL to 50 mg/mL.

24. The method according to claim 19, wherein the concentration of said glucagon-like peptide in the pharmaceutical composition is from 0.1 mg/mL to 50 mg/mL.

25. The method according to claim 1, wherein said glucagon-like peptide is GLP-2, a GLP-2 analogue, a derivative of GLP-2 or a derivative of a GLP-2 analogue.

26. The method according to claim 25, wherein said derivative of GLP-2 or a derivative of a GLP-2 analogue has a lysine residue wherein a lipophilic substituent optionally via a spacer is attached to the epsilon amino group of said lysine.

27. The method according to claim 25, wherein the concentration of said glucagon-like peptide in the pharmaceutical composition is from 0.1 mg/mL to 100 mg/mL.

28. The method according to claim 1, wherein said glucagon-like peptide is exendin-4, an exendin-4 analogue, a derivative of exendin-4, or a derivative of an exendin-4 analogue.

29. The method according to claim 28, wherein said peptide is exendin-4.

30. The method according to claim 28, wherein said peptide is a stable exendin-4 compound.

31. The method according to claim 28, wherein said peptide is a DPP-IV protected exendin-4 compound.

32. The method according to claim 28, wherein said peptide is an immunomodulated exendin-4 compound.

33. The method according to claim 28, wherein said peptide is ZP-10, i.e. $[Ser^{38}Lys^{39}]$Exendin-4(1-39) LysLysLysLysLys-amide.

34. The method according to claim 28, wherein the concentration of said peptide in the pharmaceutical composition is from 5 μg/mL to 10 mg/mL.

35. The method according to claim 1, wherein said buffer is selected from the group consisting of ortho-phosphate, TRIS, glycine, N-glycylglycine, citrate sodium acetate, sodium carbonate, glycylglycine, histidine, lysine, arginine, sodium phosphate, and sodium citrate or mixtures thereof.

36. The method according to claim 1, wherein said preservative is selected from the group consisting of phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof.

37. The method according to claim 1, wherein said pharmaceutical composition further comprises an isotonicity agent.

38. The method according to claim 37, wherein said isotonicity agent is selected from the group consisting of sodium chloride, xylitol, mannitol, sorbitol, glycerol, glucose, maltose, sucrose, L-glycine, L-histidine, arginine, lysine, isoleucine, aspartic acid, tryptophan, threonine, dimethyl sulphone, polyethyleneglycol, propylene glycol or mixtures thereof.

39. The method according to claim 1, wherein said pharmaceutical composition further comprises a surfactant.

\* \* \* \* \*

UNITED STATES PATENT AND TRADEMARK OFFICE
CERTIFICATE OF CORRECTION

PATENT NO. : 7,632,806 B2
APPLICATION NO. : 11/290634
DATED : December 15, 2009
INVENTOR(S) : Juul-Mortensen et al.

It is certified that error appears in the above-identified patent and that said Letters Patent is hereby corrected as shown below:

Column 17, Claim 20, Line 16: delete "Val8Glu$^{22}$" and insert --Val$^8$Glu$^{22}$--.

Signed and Sealed this

Twenty-fifth Day of May, 2010

David J. Kappos
*Director of the United States Patent and Trademark Office*